(12) United States Patent
Godin et al.

(10) Patent No.: US 10,780,259 B2
(45) Date of Patent: Sep. 22, 2020

(54) TAMPER EVIDENT CLOSURE ASSEMBLY

(71) Applicant: BioQ Pharma Inc., San Francisco, CA (US)

(72) Inventors: Andrew M. Godin, South San Francisco, CA (US); Ralph I. McNall, III, Belmont, CA (US); Christopher Z. Vasilas, Richmond, CA (US)

(73) Assignee: BioQ Pharma Inc., San Francisco ( * ) Notice: Subject to any disclaimer, the term of this patent is extended or adjusted under 35 U.S.C. 154(b) by 140 days.

(21) Appl. No.: 15/913,891

(22) Filed: Mar. 6, 2018

(65) Prior Publication Data
US 2019/0275313 A1 Sep. 12, 2019

(51) Int. Cl.
*A61M 39/10* (2006.01)

(52) U.S. Cl.
CPC ................ *A61M 39/1011* (2013.01)

(58) Field of Classification Search
CPC .............. A61M 39/20; A61M 39/1011; B65D 41/3409
See application file for complete search history.

(56) References Cited

U.S. PATENT DOCUMENTS

| | | | |
|---|---|---|---|
| 5,328,474 A | 7/1994 | Raines | |
| 6,003,701 A * | 12/1999 | Hidding | B65D 41/3409 215/252 |
| 6,190,364 B1 | 2/2001 | Imbert | |
| 6,394,983 B1 * | 5/2002 | Mayoral | A61M 39/20 604/192 |
| 7,198,619 B2 | 4/2007 | Bills et al. | |
| 7,648,481 B2 | 1/2010 | Geiger et al. | |
| 8,752,722 B2 | 6/2014 | Kuhn et al. | |
| 8,864,021 B1 | 10/2014 | Vitello | |
| 9,095,667 B2 | 8/2015 | Von Schuckmann | |
| 9,402,967 B1 | 8/2016 | Vitello | |
| 9,463,310 B1 | 10/2016 | Vitello | |
| 9,526,839 B2 | 12/2016 | Chia et al. | |
| 9,687,645 B2 | 6/2017 | Wesseler | |
| 2004/0064095 A1 | 4/2004 | Vitello | |
| 2008/0200881 A1 | 8/2008 | Emmott et al. | |
| 2012/0031904 A1 | 2/2012 | Kuhn et al. | |
| 2015/0165122 A1 | 6/2015 | Pommereau et al. | |
| 2017/0028186 A1 | 2/2017 | Yeh et al. | |
| 2017/0354792 A1 | 12/2017 | Ward | |

FOREIGN PATENT DOCUMENTS

GB 1483678 A 8/1977

* cited by examiner

*Primary Examiner* — Andrew T Kirsch
(74) *Attorney, Agent, or Firm* — Thomas W. Galvani, P.C.; Thomas W. Galvani

(57) ABSTRACT

A tamper evident closure assembly is for use with a fitting having an outer sidewall with internally-directed threads, externally-directed splines, and an open post. The closure assembly includes a cap, a collar, and a frangible attachment coupling the cap and collar. The cap, collar, and frangible attachment are formed integrally as an integral unit. A radial lug on the cap engages with the fitting threads. A pawl on the collar allows rotation of the integral unit on the fitting in a first rotational direction and prevents rotation in a second rotational direction. Application of the integral unit to the fitting engages the radial lug with the threads on the fitting and the post and the cap form a fluid seal. Tampering with the integral unit when the integral unit is applied to the fitting severs the frangible attachment, thereby defining the cap and collar as separate pieces.

31 Claims, 11 Drawing Sheets

TAMPER EVIDENT CLOSURE ASSEMBLY

FIELD OF THE INVENTION

The present invention relates generally to medical devices, and more particularly to medical tubing fittings.

BACKGROUND OF THE INVENTION

Tamper evident features are required for all medical devices and pharmaceutical products containing sterile components. Currently, the most common means of achieving tamper evidence for luer-type fittings is by applying a perforated shrink band over the seal area. To verify product integrity, the perforations on the band are inspected before use; any breaches in the perforations indicate that the sterility or safety of the product may be compromised. Although effective, installation of shrink bands requires secondary operations consisting of band application and a heat shrinking process, which can be both time consuming and challenging to develop. In addition to this, shrink bands can carry a wide range of quality issues related to perforation uniformity and variation in the heat shrink process, both of which may result in rejection of usable product by the manufacturer or user if the perforations inadvertently break prematurely.

Rigid tamper evident features currently available on the market commonly leave a remnant behind on the fitting once the cap is removed. This remnant can become a nuisance if it is not easily pulled off the fitting. An improved tamper evident device or feature is needed for medical tubing fittings.

SUMMARY OF THE INVENTION

A tamper evident closure assembly is for use with a fitting to seal the fitting and indicate whether the seal has been tampered. The fitting includes an outer sidewall with internally-directed threads, externally-directed splines, and a coaxial open post. The closure assembly includes a cap, a collar, and a frangible attachment coupling the cap and collar, wherein the cap, collar, and frangible attachment are formed integrally as an integral unit. A radial lug is on the cap for rotatably engaging with the threads on the fitting. A pawl is on the collar to allow rotation of the integral unit on the fitting in a first rotational direction and preventing rotation of the integral unit on the fitting in a second rotational direction. Application of the integral unit to the fitting engages the radial lug with the threads on the fitting, and the post and the cap form a fluid seal. Tampering with the integral unit when the integral unit is applied to the fitting severs the frangible attachment, thereby defining the cap and collar as separate pieces.

The above provides the reader with a very brief summary of some embodiments discussed below. Simplifications and omissions are made, and the summary is not intended to limit or define in any way the scope of the invention or key aspects thereof. Rather, this brief summary merely introduces the reader to some aspects of the invention in preparation for the detailed description that follows.

BRIEF DESCRIPTION OF THE DRAWINGS

Referring to the Drawings.

DETAILED DESCRIPTION

Figure 1:
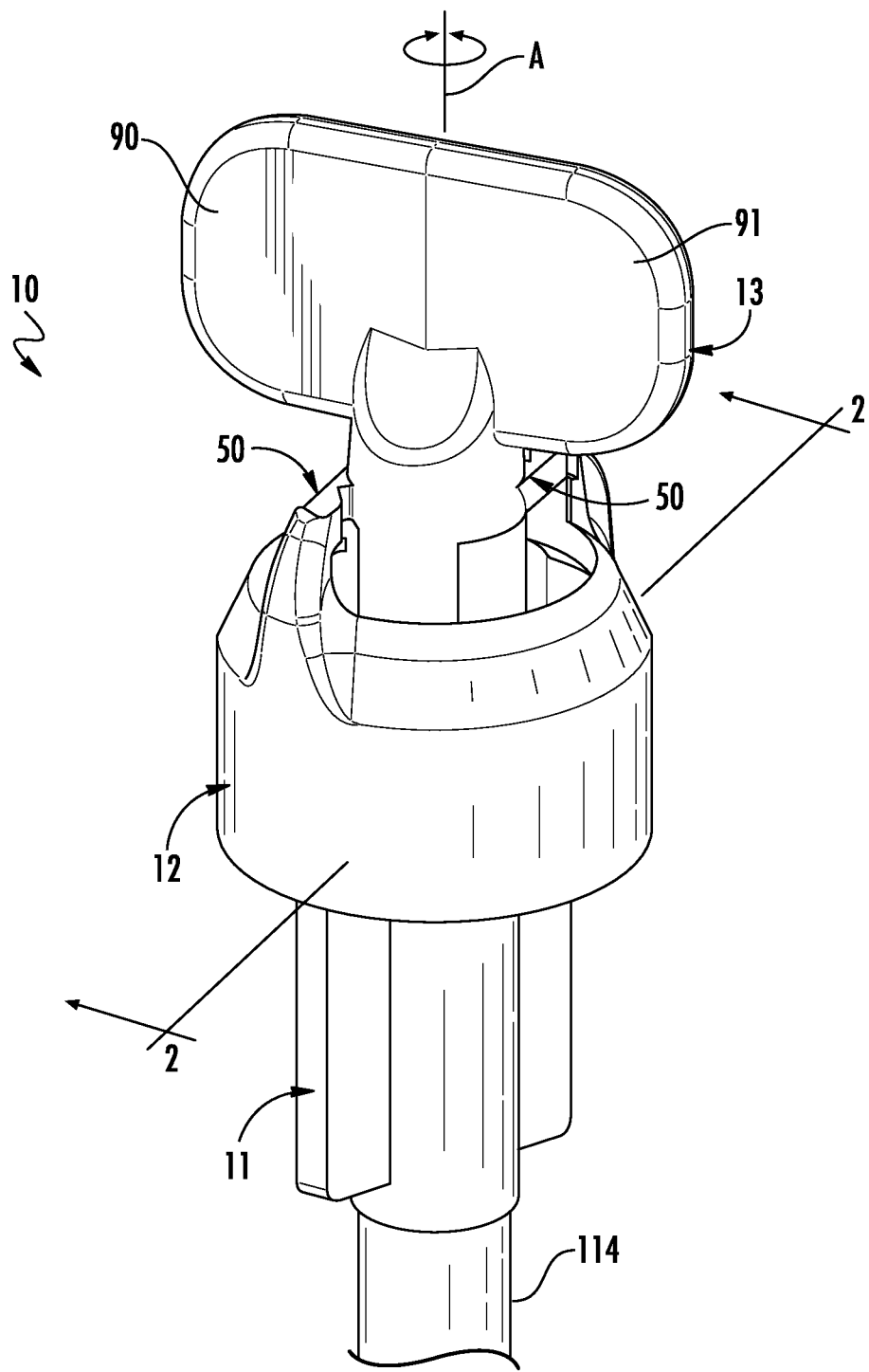
FIG. 1 is a perspective view of a tamper evident closure assembly applied to a medical tubing fitting, the assembly including a crown and a cap.

Reference now is made to the drawings, in which the same reference characters are used throughout the different figures to designate the same elements. FIG. 1 illustrates a tamper evident closure assembly 10 (hereinafter, "assembly 10") for closing a medical tubing fitting 11 (hereinafter, "fitting 11") in such a way that one can detect whether the assembly 10 has been tampered with or previously removed from the fitting 11, without a physical remnant on the fitting 11. The assembly 10 includes a crown 12 and a cap 13 attached to each other and secured on the fitting 11. The crown 12 is a roughly cylindrical structure fit over the fitting 11, having pawls which engage axial splines on the fitting 11. The crown 12 includes frangible prongs which attach the crown 12 to the cap 13. The cap 13 has radial lugs which rotatably engage with internal threads on the fitting 11. The pawl engagement and the lug engagement cooperate, when the crown 12 and cap 13 are coupled to each other, to prevent removal of the assembly 10 from the fitting 11 in both axial and rotational directions with respect to an axis A. Indeed, forcing removal in these directions will cause the prongs on the crown 12 to sever, thereby indicating that the assembly 10 has been tampered with or removed.

Figure 2A:
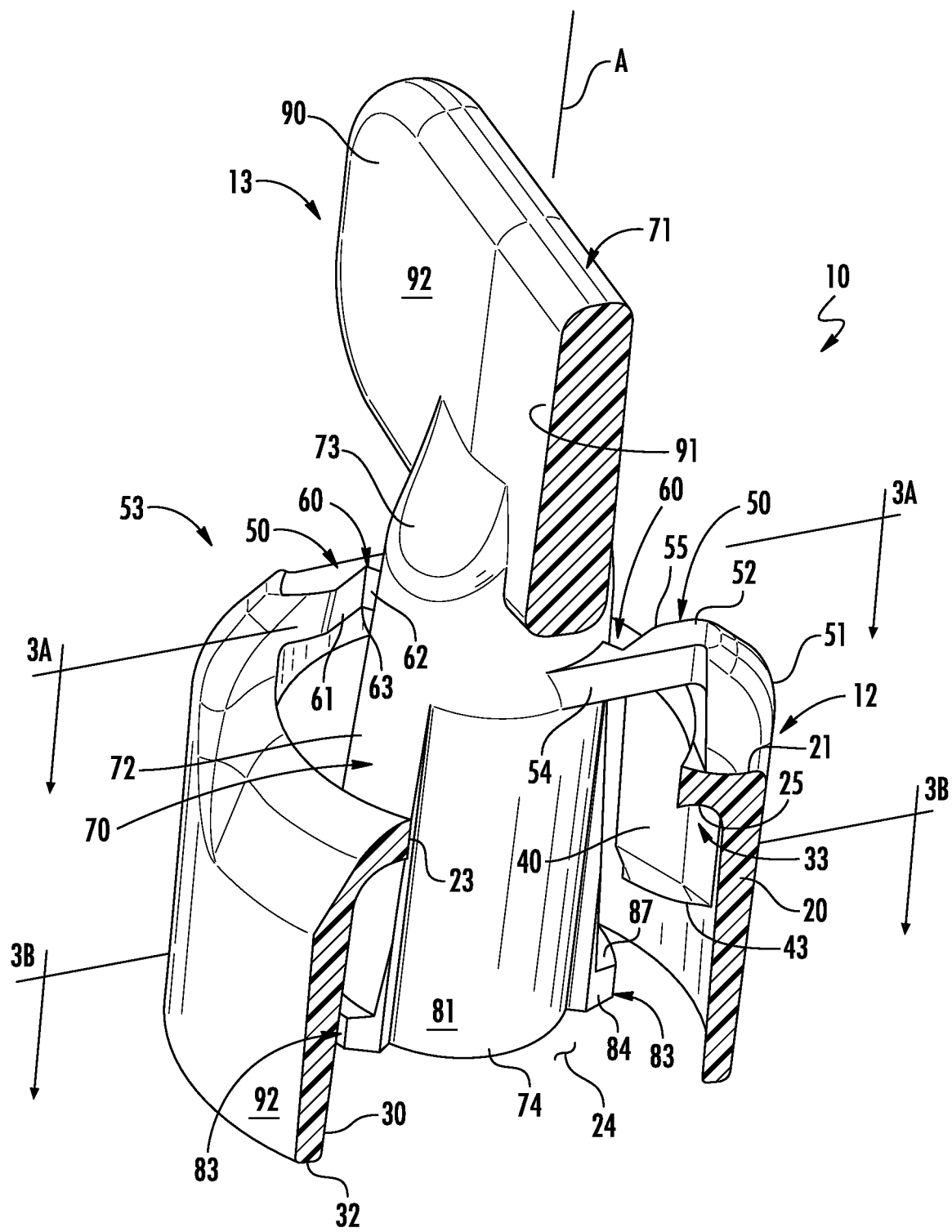
FIGS. 2A and 2B are top and bottom perspective section views, taken along the line 2-2 in FIG. 1, showing the crown and cap.
Figure 2B:
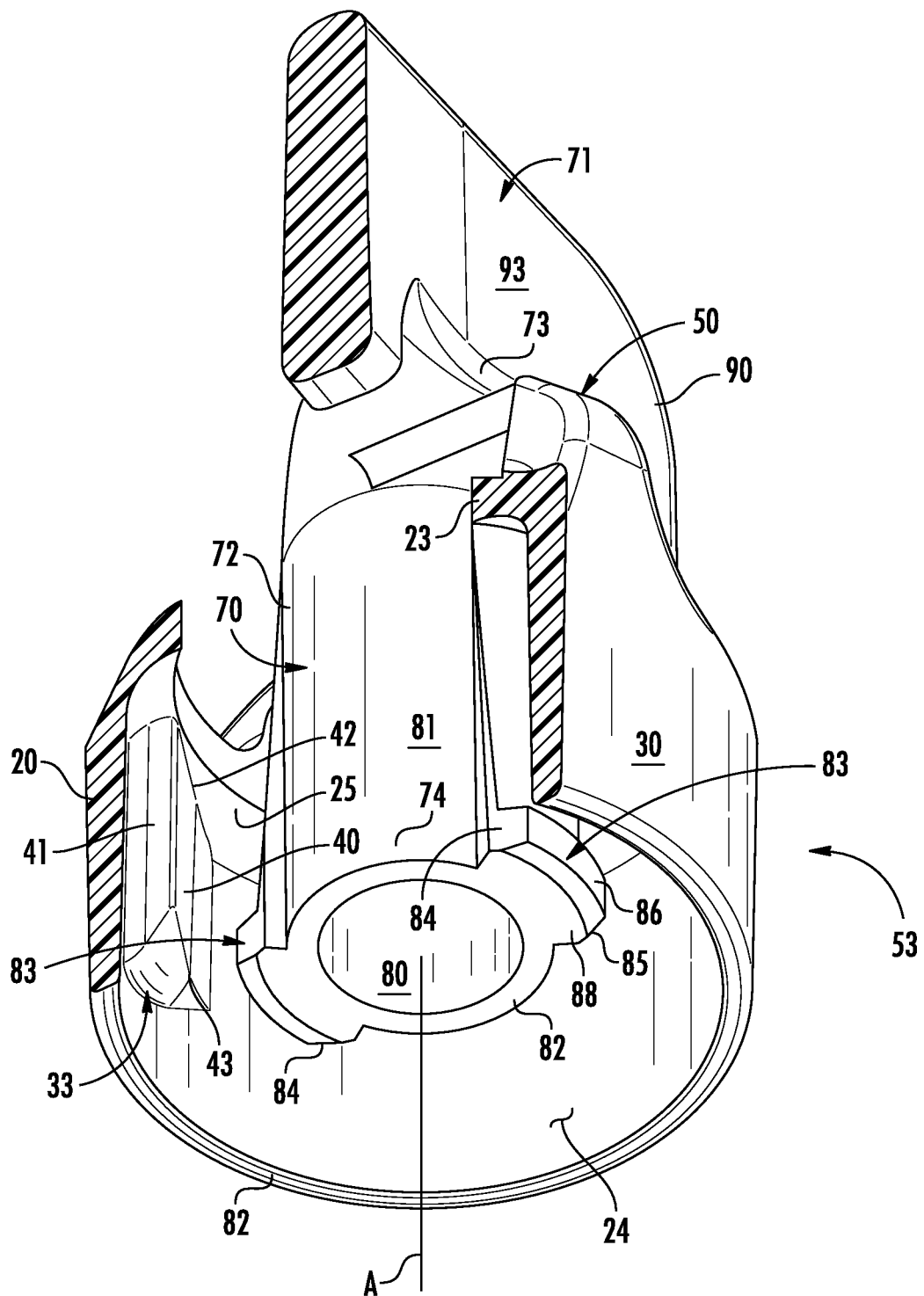

FIGS. 2A and 2B illustrate the assembly 10 in a perspective section view taken along the line 2-2 in FIG. 1, so that internal features of the crown 12 are shown. The crown 12 is a lower portion of the assembly 10; it has a generally cylindrical sidewall 20 extending between a top 21 and an opposed bottom 22. The crown 12 is open at both the top 21 and the bottom 22, so that it may be applied over the fitting 11 and so that the cap 13 can be removed from the crown 12. At the top 21, the sidewall 20 turns radially inward to form an inward lip 23. Briefly, it is noted that terms such as "radial," "inward," "outward," and "axial" are made with respect to the axis A. The lip 23, together with the cylindrical portion of the sidewall 20 and the bottom 22, bounds an interior 24 of the sidewall 20.

The sidewall 20 includes opposed inner and outer surfaces 30 and 31. The inner and outer surfaces 30 and 31 meet at a flat bottom edge 32 at the bottom 22 of the crown 12. At the top 21, the lip 23 has an underside 25 which projects radially inward from the sidewall 20, and the underside 25 forms a roughly flat annular shoulder against the inner surface 30 which extends continuously around the sidewall 20. That underside 25 is oriented approximately ninety degrees with respect to the inner surface 30 of the sidewall 20.

The outer surface 31 is substantially smooth. The inner surface 30 is also substantially smooth, but for diametrically-opposed, inwardly-directed pawls 33 formed thereon. One pawl 33 can be seen in each of FIGS. 2A and 2B. The pawls 33 are both disposed against the underside 25. The pawls 33 are identical in every respect except location, and as such, only one pawl 33 will be described herein with the understanding that the description applies equally to both pawls 33. Some of the features are shown in FIG. 2A or 2B and not the other figure. Further, it is noted that in the embodiment shown in the drawings, there are two pawls 33; in other embodiments, there is one pawl 33, and in still other embodiments there are three or more pawls 33.

The pawl 33 bulges radially inward from the inner surface 30 to serve as an interruption in the otherwise smooth inner surface 30. The pawl 33 has a ramped surface 40 and a blunt end 41. The pawl 33 is relatively tall, extending from a top 42, formed at the underside 25 of the lip 23, to a bottom 43 which is located generally intermediate with respect to the top 21 and bottom 22 of the sidewall 20. The ramped surface 40 is formed at an acute angle with respect to the inner surface 30 from which the ramped surface 40 projects; the ramped surface 40 rises from the inner surface 30 at an approximately thirty-degree angle. The blunt end 41 returns to the inner surface 30 at approximately a ninety-degree angle with respect to the ramped surface 40. These orientations can be seen in FIGS. 2A and 2B but are best depicted in the section view of FIG. 3B. The pawl 33 is positioned on the inner surface 30 such that the ramped surface 40 is in a clockwise forward direction (later defined as a first rotational direction) with respect to the blunt end 41 when viewed from a top-down perspective, as in FIG. 3B. In other words, when the crown 12 is rotated about the axis A in a clockwise direction (from the top-down perspective), an object inside the interior 24 will encounter the ramped surface 40 first and pass the blunt end 41 second. The ramped surface 40 is thus directed toward the first rotational direction and the blunt end 41 is directed in an opposite direction, toward a second rotational direction.

As shown in FIGS. 2A and 2B, the bottom 43 of the pawl 33 is also ramped. The bottom 43 of the pawl 33 is oriented axially upward and radially inward from the inner surface 30 at roughly a forty-five degree angle with respect to the vertical inner surface 30. This creates a gentle transition from the inner surface 30 to the pawl 33.

The pawls 33 are diametrically opposed, with one pawl 33 formed on the inner surface 30 opposite the other pawl 33 on the inner surface 30. As seen in FIG. 3B, the pawls 33 are integral and monolithic to the sidewall 20. The pawls 33 are hard and rigid, resistant to deflection and deformation. The sidewall 20 is thickest at the pawls 33, and the other portions of the sidewall, while also hard and rigid, deflect and deform before the pawls 33 do. Thus, as the crown 12 is rotated in a clockwise fashion, an object in the interior 24 will encounter the ramped surface 40 of the pawl 33 first, causing the sidewall 20 around the pawl 33 to deform, which pushes the pawl 33 radially outward so that the object may pass over and beyond the blunt end 41. This is explained in more detail later in the description.

Figure 3A:
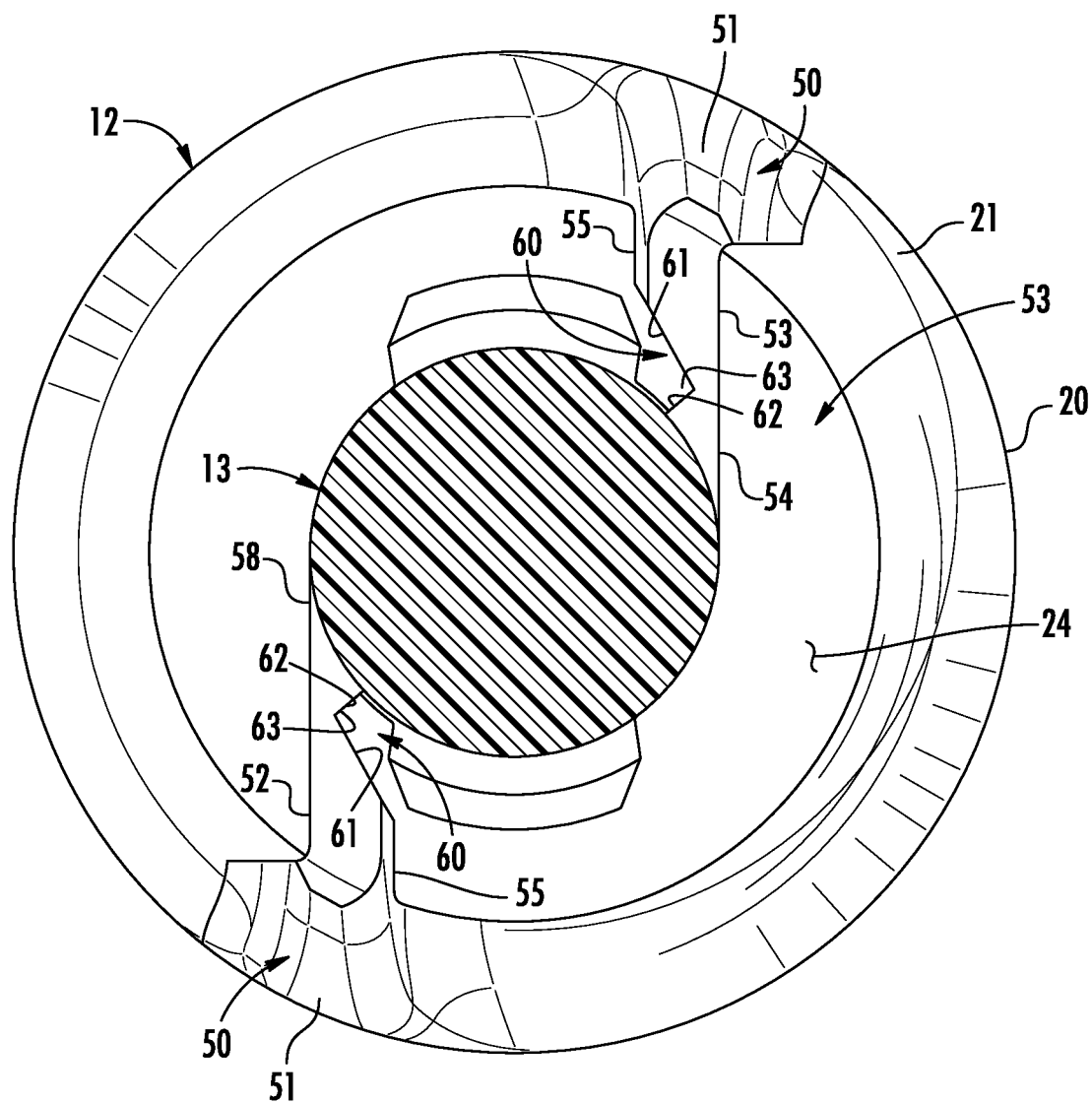
FIGS. 3A and 3B are section views taken along the lines 3A-3A and 3B-3B, respectively, in FIG. 2A.
Figure 3B:
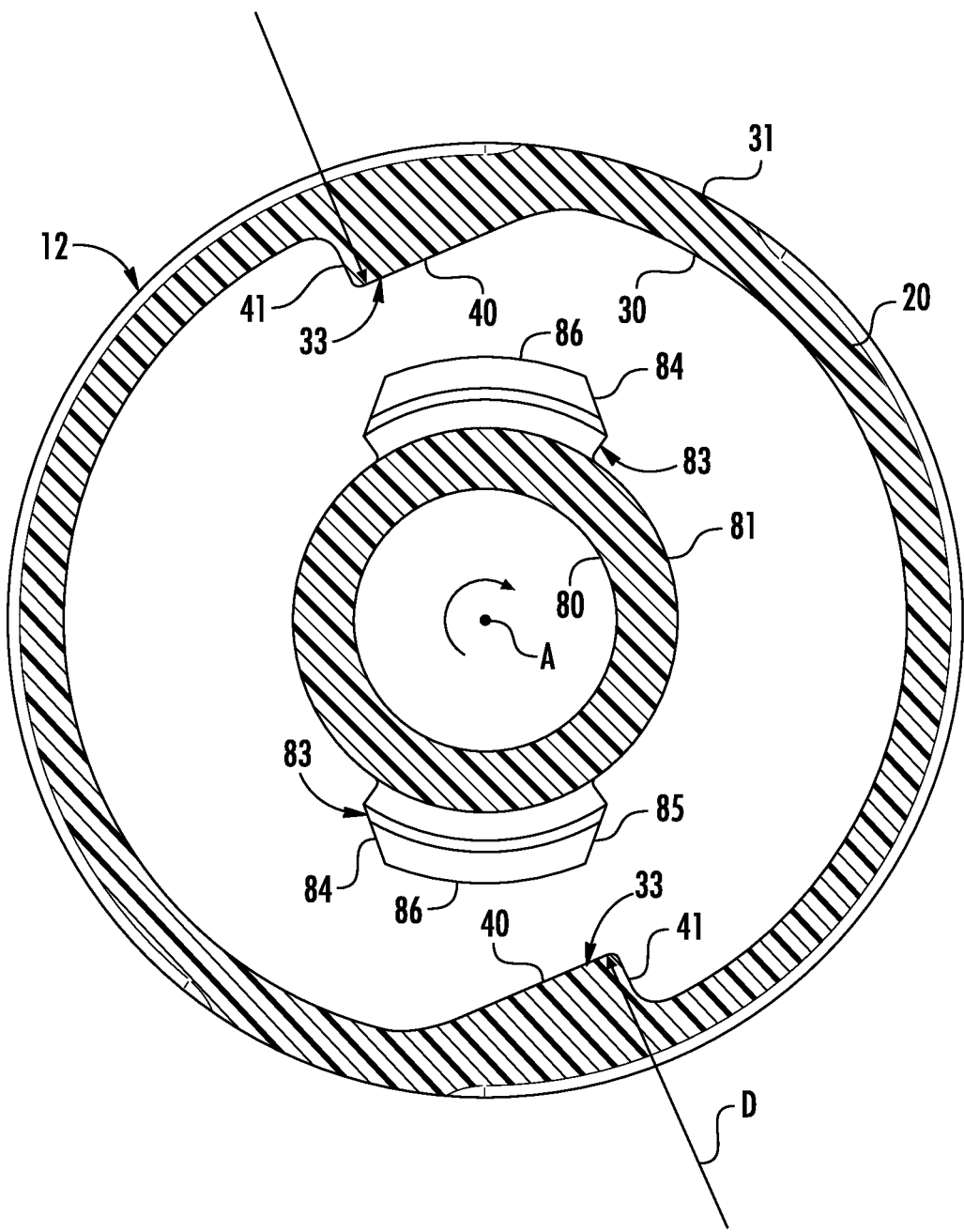

Referring primarily to FIGS. 2A and 3A, at the top 21 of the crown 12, two prongs 50 rise from the sidewall 20 and turn radially inward to connect to the cap 13. In the embodiment illustrated throughout the drawings, two prongs 50 are shown. However, other embodiments include only a single prong 50, and yet other embodiments include at least two prongs 50, such as three prongs 50, or more. The number of prongs 50 generally depends on the size of the assembly 10 and the desired necessary torque to separate the crown 12 and the cap 13. The prongs 50 shown in the illustrated embodiment are exemplary of the prongs 50 in all of these pronged embodiments. For the purposes of the embodiment shown in the figures, the prongs 50 are identical in every respect except location, and as such, only one prong 50 will be described herein with the understanding that the description applies equally to both prongs 50.

The prong 50 includes a base 51 and a lateral arm 52. The base 51 is a large protrusion extending upwardly from the top 21. The base 51 is formed integrally and monolithically to the sidewall 20, and similarly, the arm 52 is formed integrally and monolithically to the base 51. The arm 52 extends generally laterally, or radially, inward from the base 51 to the cap 13, to which it is also formed integrally and monolithically. As such, the prong 50 attaches and connects the crown 12 and cap 13, so that the crown 12, cap 13, and prong 50 are formed integrally as an integral unit 53. In other words, while the prong 50 connects the crown 12 and cap 13, the assembly 10 is intact as an integral unit 53 because the assembly 10 is a single piece. The description will thus hereinafter refer to the assembly 10 as "the integral unit 53" when the assembly 10 is intact as a one-piece unit. It will later be seen that the assembly 10 can be broken into separates pieces, so that the assembly 10 ceases to be the integral unit 53, in which case it will be identified as "the assembly 10." This does not limit the use of "the assembly 10" only to situations where it is not intact, but rather to note that generally, when intact, the assembly 10 is identified as the integral unit 53.

The arm 52 of the prong has a first side 54 and an opposed second side 55. The first side 54 is flat between the base 51 and the cap 13; the first side 54 is directed toward the clockwise forward direction, when the crown 12 is viewed from a top-down perspective. The second side 55 is contoured: it includes a notch 60 formed by first and second walls 61 and 62 oriented obliquely with respect to each other. The notch 60 extends into the arm 52, thereby reducing the thickness of the arm 52 to concentrate stress at a break point 63 between the first and second walls 61 and 62. The first and second walls 61 and 62 converge inwardly to the break point 63, which is the narrowest portion of the arm 52. The first wall 61 converges inward from proximate to the base 51; the second wall 62 converges inward from proximate to the cap 13. The notch 60 thus opens, or is concave, in the counter-clockwise direction when the crown 12 is viewed from a top-down perspective. The break point 63 is registered vertically, or parallel to the axis A.

Referring to FIGS. 1, 2A, and 2B, the cap 13 is shown attached to the crown 12 by the prongs 50. The cap 13 is an upper portion of the integral unit 53: it includes a sleeve 70 and a lobed handle 71 attached to the sleeve 70. The sleeve 70 and handle 71 are integrally, monolithically, and rigidly formed to each other, such that movement of one imparts direct movement to the other.

The sleeve 70 has a generally truncated cone-shaped sidewall 72 which extends between a top 73 of the sleeve 70 and a bottom 74 of the sleeve 70. The sleeve 70 is open at the bottom 74 but closed at the top 73, so that it may be applied over the fitting 11 to form a fluid seal 14 with the fitting 11 (it is noted here that "fluid seal 14," shown in FIG. 6, includes both a liquid-impervious seal and a gas-impervious seal). The sidewall 72 has opposed inner and outer surfaces 80 and 81, which meet at a flat bottom edge 82. In this embodiment, the bottom edge 82 of the sleeve 70 is not level or co-planar with the bottom edge 32 of the crown 12, but is instead above the bottom edge 32. Both the inner and outer surfaces 80 and 81 taper inwardly from the bottom 74 to the top 73, giving the sleeve 70 its slight conical shape. The inner surface 80 of the sleeve 70 is smooth and uninterrupted; when the cap 13 is applied to the fitting 11, the inner surface 80 of the sleeve 70 snug-fits onto the post of the fitting 11 to fluid seal the post. The outer surface 81 is formed with two diametrically-opposed radial lugs 83 formed thereon. The lugs 83 are identical in every respect except location, and as such, only one lug 83 will be described herein with the understanding that the description applies equally to both lugs 83. Further, it is noted that in the embodiment shown in the drawings, there are two lugs 83; in other embodiments, there is one lug 83, and in still other embodiments there are three or more lugs 83.

The lug 83 projects radially outward from the outer surface 81 of the bottom 74 of the sleeve 70 to serve as an engagement with threads on an inner surface of the fitting 11. The lug 83 has opposed sides 84 and 85, an outside edge 86, and a top 87 and bottom 88. The bottom 88 is contiguous to the bottom edge 82 of the sleeve 70. The lug 83 extends around an arc portion of the outer surface 81, but not entirely around the outer surface 81: the two lugs 83 are circumferentially spaced apart from each other. The lug 83 projects radially outward from the outer surface 81 to the outside edge 86 which is arcuate and coaxial to the outer surface 81. The sides 84 and 85 are not aligned radially; they are instead oblique with respect to the outer surface 81 and shape the lug 83 as a slightly tapered wedge. Further, the top 87 is tapered downward, and there is a slight bevel from the bottom 88 to the outside edge 86. As such, the lug 83 tapers slightly in height from the outer surface 81 to the outside edge 86.

The lugs 83 are diametrically opposed: one lug 83 is formed on the outer surface 81 opposite the other lug 83 on the outer surface 81. The lugs 83 are integral and monolithic to the sidewall 72 of the sleeve 70. The lugs 83 are hard, rigid, and unyielding, as is the sidewall 72. Thus, as the cap 13 is rotated around in a clockwise fashion, the lugs 83 encounter internal threads of the fitting 11 and guide rotation of the cap 13 according to the threads. When the integral unit 53 is intact, the lugs 83 are axially below the pawls 33, and are axially spaced-apart from the pawls 33 with the tops 87 of the lugs 83 axially below the bottoms 43 of the pawls 33.

Opposite the lugs 83, at the top of the cap 13, is the handle 71. The handle 71 extends upwardly and laterally from the top 73 of the sleeve 70 into two opposed lobes 90 and 91. The lobes 90 and 91 are directed away from each other, and opposed major contact faces 92 and 93 extend across both of the lobes 90 and 91. The lobes 90 and 91 are hard and rigid, and they provide a location at which a user can grasp the handle 71 and rotate the cap 13.

Figure 4:
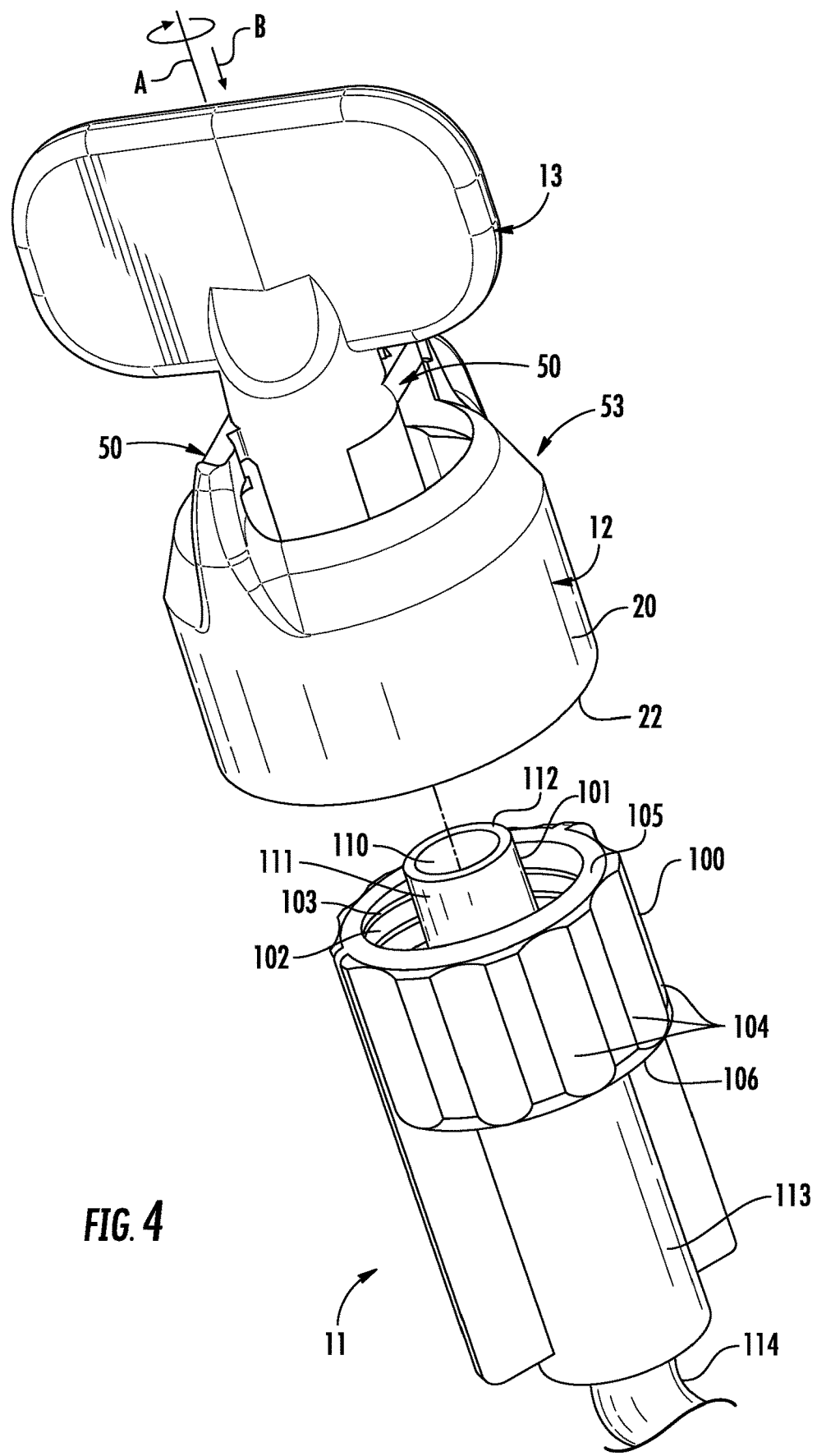
FIGS. 4-6 are top perspective views illustrating steps of applying the tamper evident closure assembly to the fitting.
Figure 5:
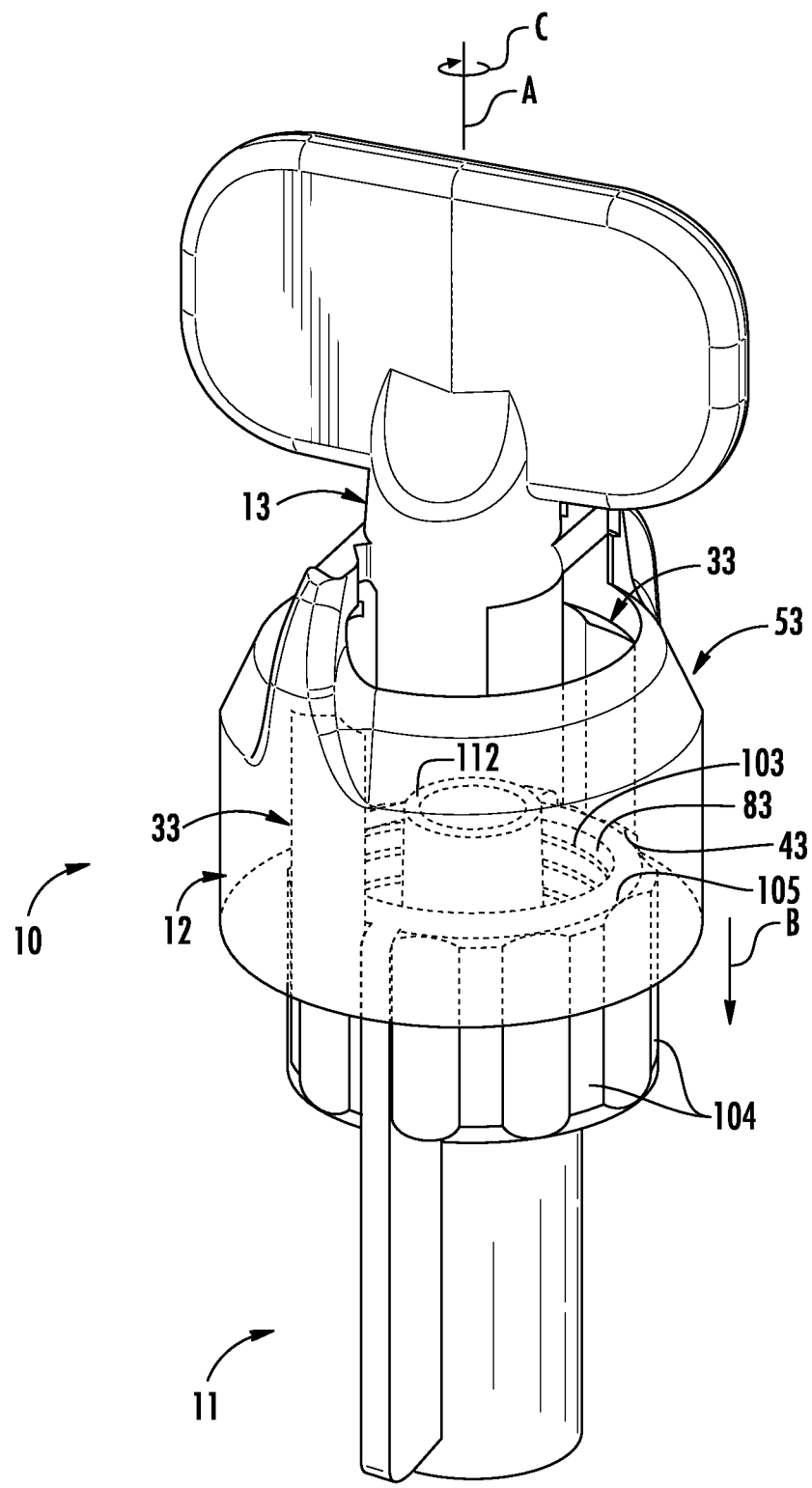
Figure 6:
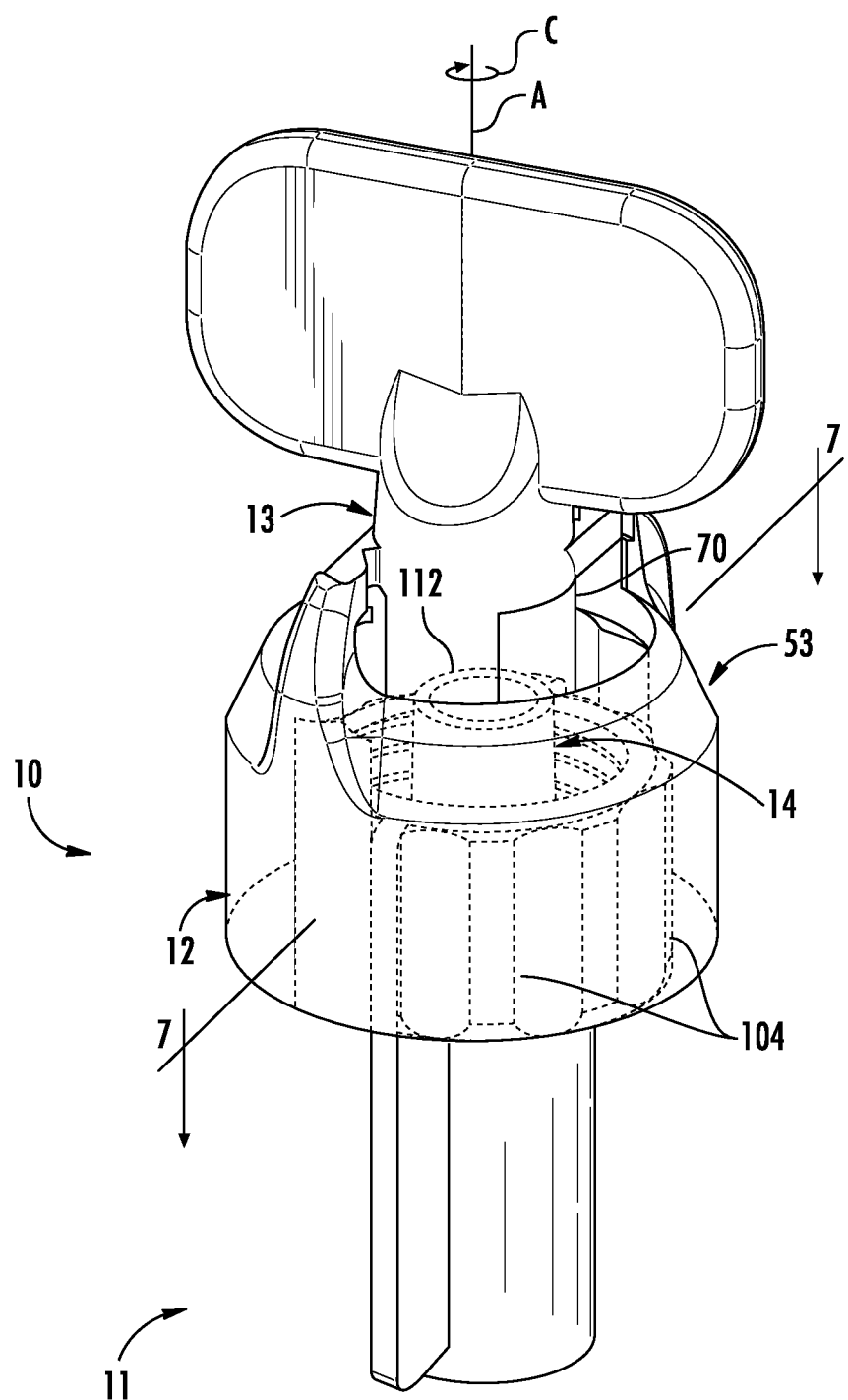

In operation, the integral unit 53 is useful for closing and fluid sealing a sterile medical tubing fitting 11, shown in FIGS. 4-6. The fitting 11 includes an outer, upstanding cylindrical sidewall 100 and an inner coaxial post 101. The sidewall 100 has an inner surface 102 carrying internally-directed threads 103. The threads 103 are hard, rigid, and unyielding, to rigidly define a helical course along the inner surface 102. The sidewall 100 has an outer surface formed with vertical or axial splines 104, which are radially-projecting, axially-oriented ribs protruding outward from the outer surface of the sidewall 100. The splines 104 are hard, rigid, and unyielding, as is the sidewall 100 of the fitting 11. The sidewall 100 has an open top 105 and a closed bottom 106. The post 101 is cylindrical and has smoother inner and outer surfaces 110 and 111. The post 101 has an open top 112 and an opposed open bottom proximate the bottom 106 of the sidewall 100. The post 101 is open from the top 112 to its bottom because it is a fluid port; the post 101 is formed in fluid communication with a hollow-bore stem 113. In some embodiments, the stem 113 is formed to a tubing set 114 (as in FIGS. 1 and 4) for connecting to an instrument, while in other embodiments, the stem 113 is the terminal portion of the fitting 11 and may be later fitted or assembled to a tubing set or some other device. It is noted here that FIGS. 1 and 4 are the only figures which show the tubing set 114, as one having ordinary skill in the art will readily understand how the tubing set 114 may or may not be connected to the fitting 11.

The integral unit 53 is typically applied to the fitting 11 during assembly by the manufacturer, but in some cases, the integral unit 53 may be applied to the fitting 11 by a medical professional after the fitting 11 is sterilized. Once applied to a sterilized fitting 11, the integral unit 53 maintains the sterility of the fitting 11 until it is removed therefrom. A health worker coming upon the integral unit 53 can immediately discern whether the assembly 10 has been tampered with; if someone has removed or attempted to remove the assembly 10 such that the sterility of the fitting 11 could have been exposed to contamination, then the prongs 50 will be severed, and the integral unit 53 of the assembly 10 will be compromised.

To apply the integral unit 53 to the fitting 11, the integral unit 53 is taken up and the bottom 22 of the crown 12 is directed toward the top of 105 of the sidewall 100. The inner surface 30 of the sidewall 20 of the crown 12 is registered with the outer surface of the fitting 11 formed with the splines 104, and the inner surface 80 of the sidewall 72 of the cap 13 is registered with the outer surface 111 of the post 101. Once so registered, the integral unit 53 is then applied onto the fitting by moving the integral unit 53 downward in the direction indicated by the arrowed line B in FIG. 4 while also rotating the integral unit 53 in the direction indicated by the arcuate arrowed line C about the axis A (a "first" rotational direction). Because the integral unit 53 is intact, application of a downward rotational force to the cap 13 acts to move the entire integral unit 53 correspondingly.

This movement partially applies the integral unit 53 to the fitting 11, as shown in FIG. 5. As the integral unit 53 is moved downward and rotated, the lugs 83 of the cap 13 engage with the internal threads 103 on the sidewall 100. This guides rotation of the integral unit 53 with respect to the fitting 11. The integral unit 53 rotates, causing the integral unit 53 to move downward over the fitting 11, until the bottom 43 of the pawls 33 reach the top 105 of the sidewall 100 of the fitting 11. The pawls 33 are separated by an inner diameter D (shown in FIG. 3B) which is just larger than the outer diameter of the sidewall 100, but is not larger than the outer diameter measured across the sidewall 100 between opposing splines 104. As such, the integral unit 53 is prevented from further rotational movement by interaction of the pawls 33 against the splines 104 unless greater force is applied.

In the partially-installed state shown in FIG. 5, the fitting 11 is not yet fluid sealed by the integral unit 53. There is a small gap between the top 112 of the post 101 and the inner surface 80 of the sleeve 70. That inner surface 80 is tapered; the inner diameter of the sleeve 70 is larger at the bottom 74 of the sleeve 70 than it is just below the closed top 73, so that as the top 112 of the post 101 is moved further up into the sleeve 70, it contacts and fluid seals the inner surface 80. However, in the state shown in FIG. 5, the top 112 does not yet contact or fluid seal the inner surface 80. The integral unit 53 can still also be non-destructively removed from the fitting 11: removal is accomplished by rotating the integral unit 53 backwards, in opposition to the arrowed line C of FIG. 4 (a "second" rotational direction), without destroying and separating the intact integral unit 53 into the crown 12 and cap 13.

To more fully apply the integral unit 53, the integral unit 53 is rotated in the first rotational direction, causing the pawls 33 to move downward and in the first rotational direction, over the splines 104. Once the pawls 33 are moved over the splines 104, the integral unit 53 cannot be non-destructively removed from the fitting 11: engagement of the pawls 33 with the splines 104 prevents rotation of the integral unit 53 in the second rotational direction, and forced rotation in the second rotational direction will operate to destroy and separate the intact integral unit 53 into the crown 12 and cap 13. To move the integral unit 53 further onto the fitting 11 so that the pawls 33 are moved over the splines 104, more force is applied in the first rotational direction of line C while the integral unit 53 is pushed downward along the line B. This advances the splines 104 against the ramped surface 40 of the pawls 33. Because the ramped surface 40 is ramped inwardly, and because the spline 104 and the sidewall 100 of the fitting 11 are hard, rigid, and unyielding, a contact force is produced between the pawl 33 and the spline 104, tending to urge the spline 104 inward and the pawl 33 outward. The sidewall 20 to which the pawl 33 is formed is moved outward; the sidewall 20 bows slightly so that the spline 104 may pass over the pawl 33. It does so until it reaches the blunt end 41, at which point the sidewall 20 stops bowing and returns to its original configuration. However, the integral unit 53 continues to be rotated, and so the pawls 33 successively move against and over each spline 104 in this fashion, allowing the integral unit 53 to move further forward in a clockwise rotational direction and further downward on the fitting 11 until the post 101 and the cap 13 for the fluid seal 14. The pawls 33 are disposed among the splines 104 when the post and the cap form the fluid seal 14, and so the integral unit 53 cannot be removed from the fitting 11 without breaking the fluid seal 14 and without separating the integral unit 53. Advancement of the integral unit 53 is continued until the integral unit 53 is fully seated on the fitting 11.

Figure 7:
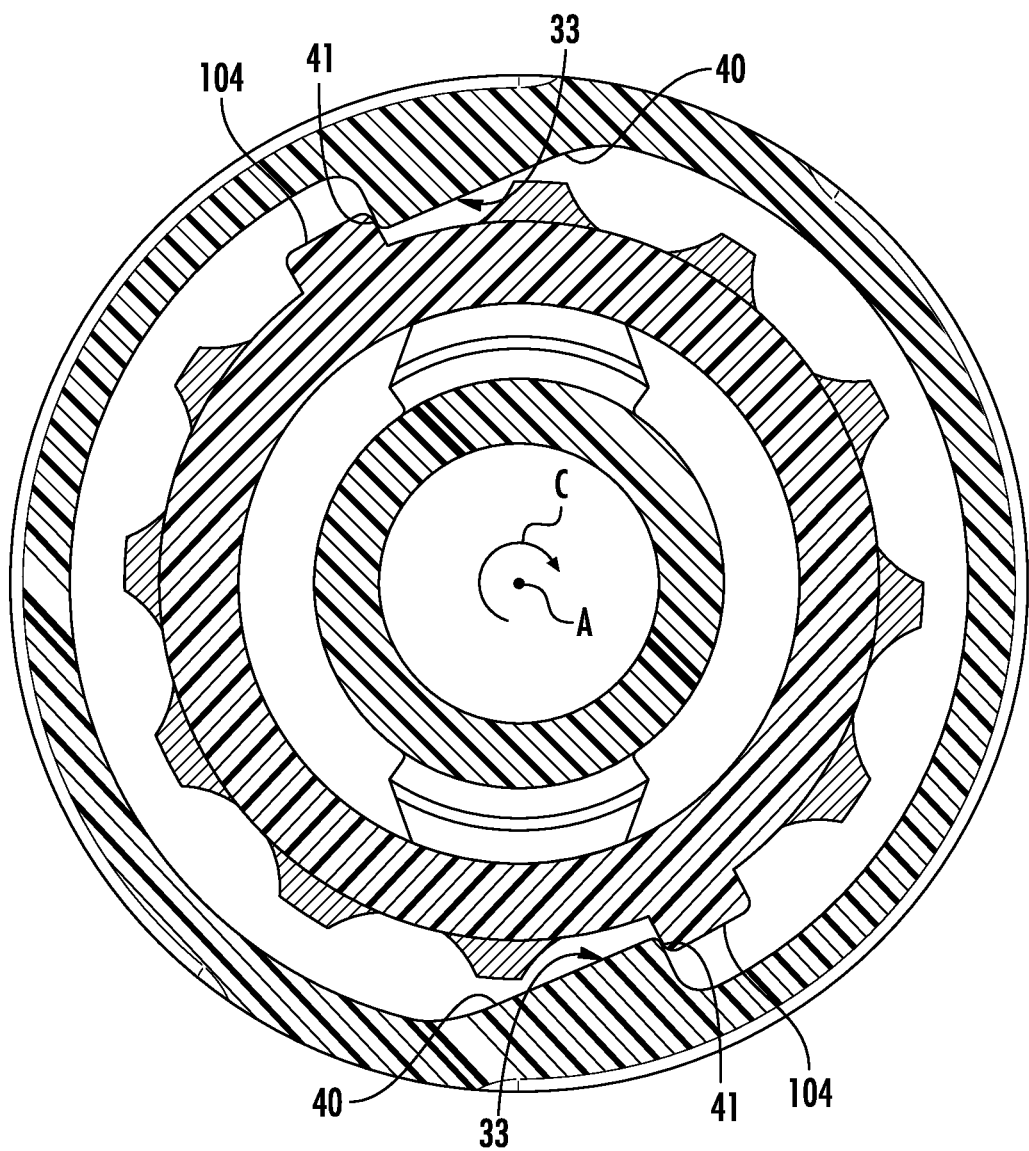
FIG. 7 is a section view taken along the line 7-7 in FIG. 6 showing an engagement of the tamper evident closure assembly with the fitting.

When the integral unit 53 is fully seated on the fitting 11, it can be advanced axially no further, and the top 112 of the post 101 is still in direct and fluid-sealing contact with the inner surface 80 of the sleeve 70. As such, the integral unit 53 securely closes and fluid seals the fitting 11. FIG. 6 illustrates this state. The pawls 33 are disposed between splines 104 against the outer surface of the sidewall 100. FIG. 7, a section view taken along the line 7-7 of FIG. 6, shows the blunt end 41 of each pawl 33 against the sides of the splines 104. Further forward movement of the crown 12 around the axis A in the first rotational direction of arrowed line C is no longer possible without separating the crown 12 from the cap 13 because the bottom edge 82 of the sleeve 70 of the cap 13—to which the crown 12 is formed as the integral unit 53—is fully seated into the fitting 11, thereby preventing further axial movement downward and thus also further helical movement. However, the crown 12 also cannot be rotated in opposition to the first rotational direction of arrowed line C without separation from the cap 13; interaction of the blunt ends 41 with the splines 104 prevents this. Because the blunt end 41 is oriented nearly parallel to the side of the spline 104, application of torque about the axis A in the second rotational direction opposite to the arrowed line C does not cause the spline 104 to slip over and beyond the pawl 33 as it does in the other direction.

The crown 12 thus cannot be non-destructively rotated in the first or second rotational directions, i.e., with or in opposition to the arrowed line C, and, correspondingly, the integral unit 53 cannot be non-destructively rotated in the first or second rotational directions, i.e., with or in opposition to the arrowed line C. In other words, when fully applied to the fitting 11, the integral unit 53 is prevented from rotational movement in both clockwise and counter-clockwise directions by engagement of the pawls 33 with the splines 104, while the crown 12 remains coupled to the cap 13 by the prongs 50, i.e., while the integral unit 53 is intact.

Further, when the integral unit 53 is fully seated on the fitting 11 as in FIG. 6, it cannot be advanced or retracted along the axis A. Interaction of the bottom edge 82 of the sleeve 70 of the cap 13 with the closed bottom 106 of the fitting 11 prevents downward axial movement of the cap 13. The engagement of the lugs 83 of the cap 13 with the threads 103 on the inner surface 102 of the sidewall 100 allows only rotational or helical movement of the cap 13 with respect to the fitting 11. However, because the cap 13 cannot rotate, as described above, it cannot move in a helical fashion and thus cannot translate axially. And the engagement of the lugs 83 with the threads 103, both of which are hard, rigid, and unyielding, prevents the cap 13 from being directly axially withdrawn from the fitting 11.

Thus, the cap 13 is prevented from downward axial movement and from upward axial movement. The integral unit 53 cannot be non-destructively advanced or retracted along the axis A. In other words, when fully applied to the fitting 11, the integral unit 53 is prevented from axial movement in both forward and rearward directions by engagement of the lugs 83 with the threads 103, while the crown 12 remains coupled to the cap 13 by the prongs 50, i.e., while the integral unit 53 is intact.

However, the prongs 50 are frangible attachments; they are designed to break under force. Here, "frangible" means designed to break, as distinguished from capable of breaking. When the prongs 50 are severed, the crown 12 and cap 13 are severed into separate pieces and the integral unit 53 is eliminated. A user can sever the prong 50 by rotating the cap 13 in the second rotational direction to cause the prong 50 to bend backward at the break point 63.

Only the cap 13 forms the fluid seal 14 with the post 101 of the fitting 11. The crown 12 maintains security of the cap 13 on the fitting 11. A user can detect that the assembly 10 has been tampered with because the frangible attachments between the crown 12 and cap 13—the prongs 50—are severed. The prongs 50 are disposed above the crown 12 are thus visible from outside the assembly 10. Tampering is defined as any action which compromises the fluid seal 14 formed between the assembly 10 and the fitting 11. Typically, the fluid seal 14 is compromised by retracting the cap 13 an axial distance such that the top 112 of the post 101 breaks contact with the inner surface 80 of the sleeve 70. This cannot occur without separating the integral unit 53 into the crown 12 and cap 13.

Figure 8:
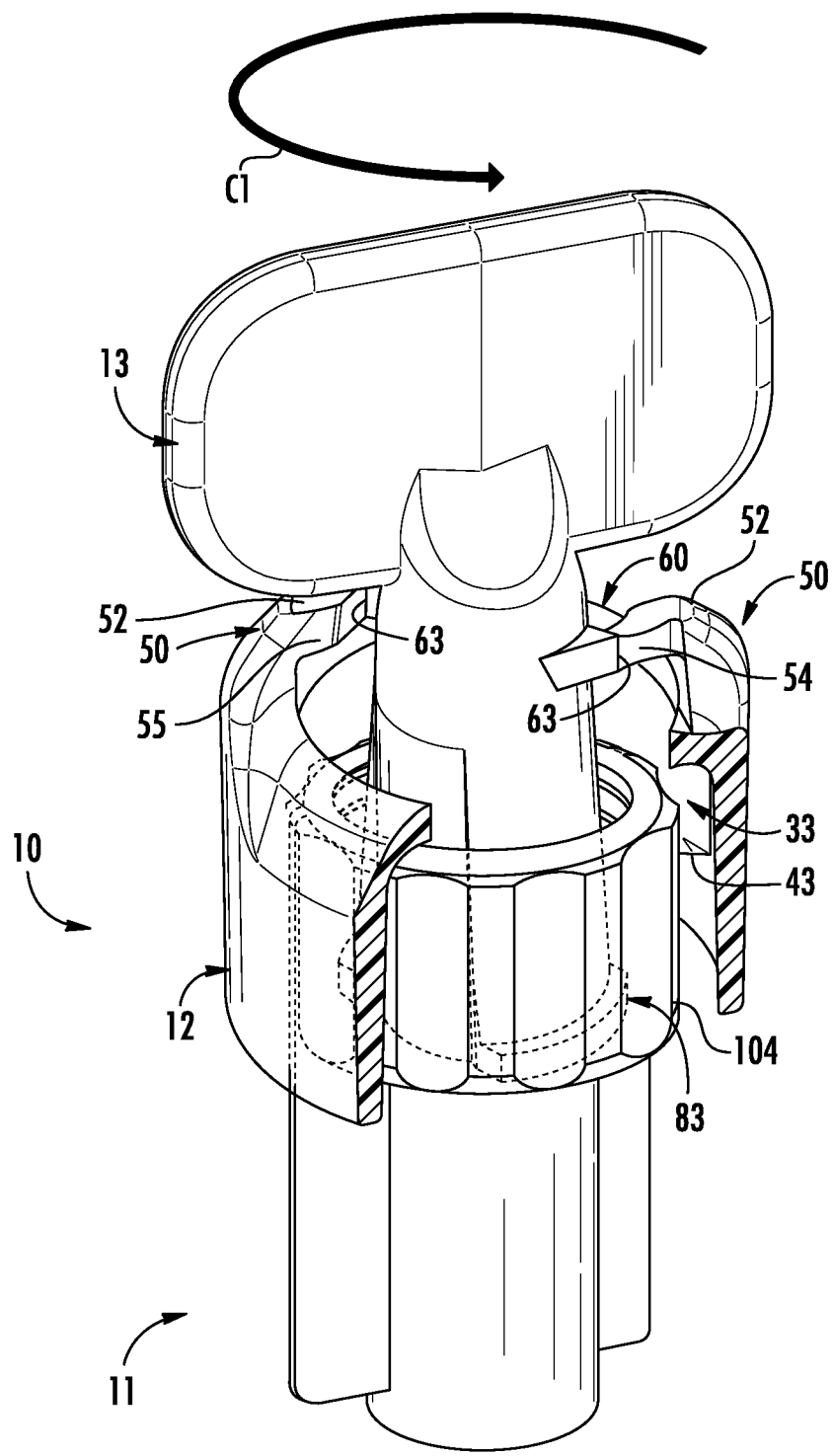
FIGS. 8 and 9 are top perspective, partial-section views, taken along the line 2-2, showing removal of the tamper evident closure assembly from the fitting.
Figure 9:
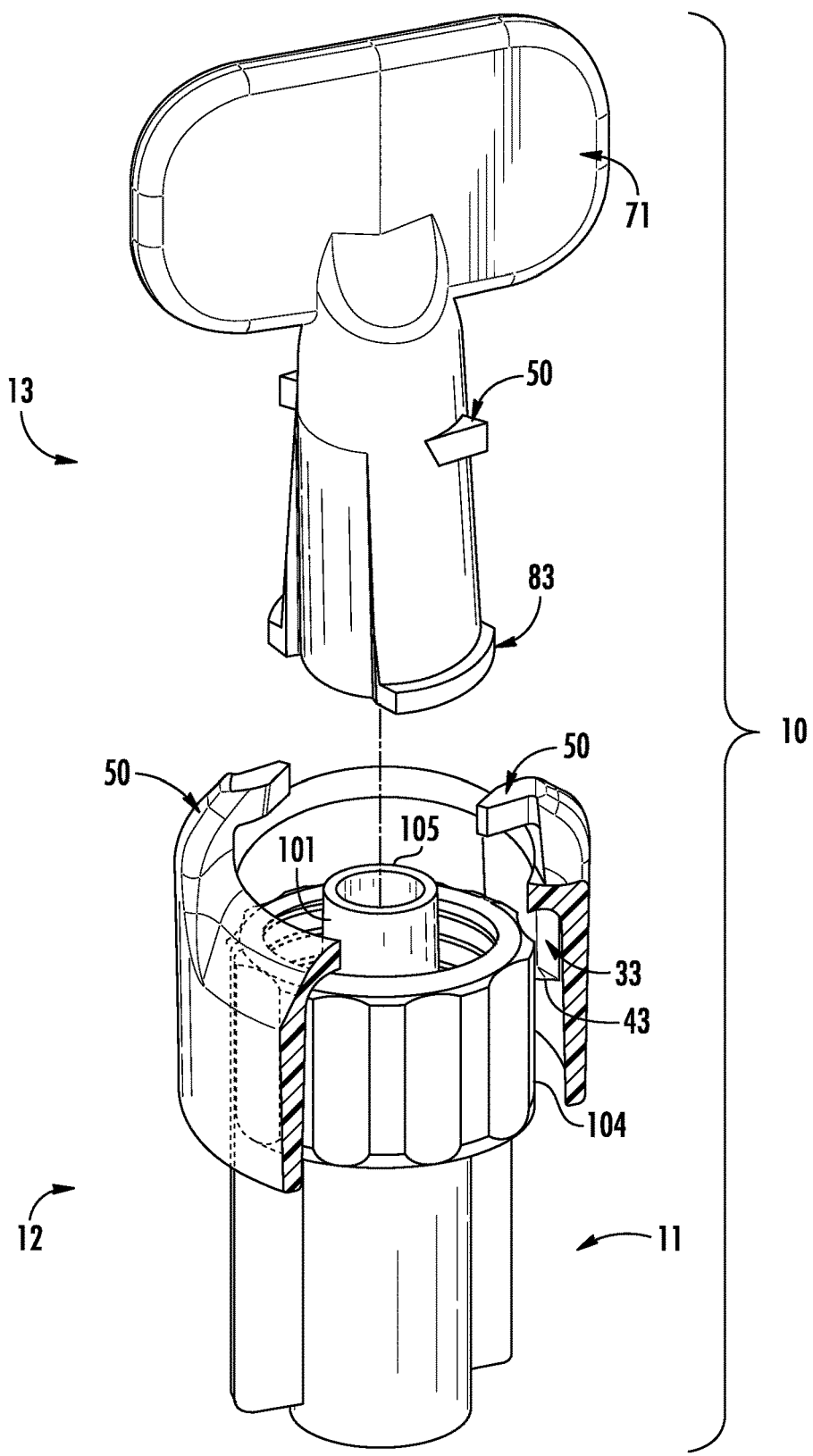

Once the integral unit 53 is applied to the fitting 11, application of a rotation force or torque on the crown 12 or the cap 13 in the second rotational direction causes the blunt ends 41 to bear against the splines 104 of the fitting 11. This prevents the crown 12 from rotating, and so the user cannot grab and twist the crown 12 backward. However, if the user grabs the handle 71 of the cap 13 and rotates the cap 13 in the second rotational direction (indicated by the arrowed line C' in FIG. 8), then the cap 13 tends to move slightly upward along the axis A and also slightly toward the second rotational direction. This causes the prongs 50 to buckle backward, such that the first side 54 of the arm 52, which is normally flat and straight, begins to buckle. On the opposite second side 55 of the arm 52, the notch 60 opens up, widening about the break point 63. Continued application of torque to the handle 71 in the second rotational direction continues to buckle the prongs 50. The crown 12 is prevented from movement in the second rotational direction by the engagement of the pawls 33 with the splines 104. However, the cap 13 can continue to move slightly upward and toward the second rotational direction. Thus, the cap 13 moves with respect to the crown 12 until the prongs 50 tear and break at the break point 63.

Once the prongs 50 are severed, the integral unit 53 is destroyed: the assembly 10 is redefined as a crown 12, a separate cap 13, and pieces of the severed prongs 50 on both the crown 12 and cap 13.

The prongs 50 are configured to sever in response to movement of the cap 13 with respect to the crown 12 in a certain fashion. The prongs 50 sever when the crown 12 and cap 13 are in particular axial and rotational orientations with respect to each other, because an amount of longitudinal stretching and bending is required to sever the prongs 50. This occurs when the top 112 of the post 101 of the fitting 11 breaks contact with the inner surface 80 of the sleeve 70 of the cap 13, because the cap 13 has risen axially.

When the cap 13 axially retracts from the fitting 11 a distance sufficient to break the fluid seal 14 between the post 101 and the sleeve 70 of the cap 13, the prongs 50 sever. Before the cap 13 retracts this distance, the fluid seal 14 between the post 101 and the sleeve 70 is maintained, and the prongs 50 are not severed. As such, it is only when the fluid seal 14 is broken that the prongs 50 are also broken. Because of this, separation of the prongs 50 indicates that the fluid seal 14 has been compromised; a user who finds the prongs 50 severed can quickly determine that the fluid seal 14 of the assembly 10 has been compromised, and that the fitting 11 may no longer be sterile. And conversely, a user who finds the integral unit 53 fully installed on the fitting 11 and the prongs 50 intact can quickly determine that the fluid seal 14 of the integral unit 53 is also intact, and that the fitting 11 remains sterile.

If the user finds the integral unit 53 fully installed on the fitting 11 and the prongs 50 intact, then the user removes the integral unit 53 to use the fitting 11. The integral unit 53 is first separated into constituent crown 12 and cap 13 via the method described above. Once the cap 13 has been so separated from the crown 12, the cap 13 is removed from the fitting 11: the crown 12 cannot be removed until the cap 13 is. The cap 13 is merely rotated in the second rotation direction to back the lugs 83 through the threads 103 of the fitting 11 until the cap 13 is free. Once the cap 13 is removed, the crown 12 can be easily retracted axially from the fitting 11: the pawls 33 guide axial sliding of the crown 12 off the fitting 11, and indeed, the crown 12 usually simply loosely falls off the fitting 11 once the cap 13 has been removed. Of course, once the separated crown 12 and cap 13 are removed from the fitting 11, they are discarded. They do not remain on the fitting 11. They are not used again, as they can no longer indicate that a fitting 11 to which they might be applied is sterile.

A preferred embodiment is fully and clearly described above so as to enable one having skill in the art to understand, make, and use the same. Those skilled in the art will recognize that modifications may be made to the description above without departing from the spirit of the invention, and that some embodiments include only those elements and features described, or a subset thereof. To the extent that modifications do not depart from the spirit of the invention, they are intended to be included within the scope thereof.

The invention claimed is:

1. A tamper evident closure assembly for use with a fitting, the fitting including an outer sidewall with internally-directed threads, externally-directed splines, and a coaxial open post, the closure assembly comprising:
   a cap, a crown encircling the cap and spaced apart from the cap, and a frangible attachment extending between the cap and the crown and coupling the cap to the crown, wherein the cap, crown, and frangible attachment are formed integrally as an integral unit;
   a radial lug on the cap for rotatably engaging with the threads on the fitting, wherein the radial lug is positioned below the frangible attachment;
   a pawl on the crown for allowing rotation of the integral unit on the fitting in a first rotational direction and preventing rotation of the integral unit on the fitting in a second rotational direction;
   wherein application of the integral unit to the fitting engages the radial lug with the threads on the fitting, and the post and the cap form a fluid seal; and
   tampering with the integral unit when the integral unit is applied to the fitting severs the frangible attachment, thereby defining the cap and crown as separate pieces.

2. The tamper evident closure assembly of claim 1, wherein the frangible attachment is a prong including a base formed on the crown and a lateral arm extending from the crown to the cap.

3. The tamper evident closure assembly of claim 2, wherein the frangible attachment includes at least two prongs, each including a base formed on the crown and a lateral arm extending from the crown to the cap.

4. The tamper evident closure assembly of claim 2, wherein the prong includes a notch configured to break when the integral unit is tampered.

5. The tamper evident closure assembly of claim 4, wherein the notch is oriented laterally toward the second rotational direction.

6. The tamper evident closure assembly of claim 1, wherein rotation of the cap in the second rotational direction, while the integral unit is intact, severs the frangible attachment.

7. The tamper evident closure assembly of claim 1, wherein the frangible attachment is configured to sever when the cap moves relative the fitting such that the fluid seal is tampered.

8. The tamper evident closure assembly of claim 1, further comprising an inner surface of the cap which is conically tapered from a bottom of the cap toward a top of the cap.

9. The tamper evident closure assembly of claim 1, wherein during application of the integral unit to the fitting, the pawl is disposed among the splines when the post and the cap form a fluid seal.

10. The tamper evident closure assembly of claim 1, wherein the pawl includes:
    a ramped surface oriented acutely with respect to an inner surface of the crown;
    a blunt end extending back from the ramped surface toward the inner surface of the crown transverse to the ramped surface; and
    the ramped surface is directed toward the first rotational direction and the blunt end is directed toward the second rotational direction.

11. The tamper evident closure assembly of claim 1, wherein the frangible attachment is visible from outside of the assembly.

12. A tamper evident closure assembly for use with a fitting, the fitting including an outer sidewall with internally-directed threads, externally-directed splines, and a coaxial open post, the closure assembly comprising:

a cap, a crown encircling the cap and spaced apart from the cap, and a frangible attachment extending between the cap and the crown and coupling the cap anitto the crown, wherein the cap, crown, and frangible attachment are formed integrally as an integral unit;

a radial lug on the cap for rotatably engaging with the threads on the fitting, wherein the radial lug is positioned below the frangible attachment;

a pawl on the crown for allowing rotation of the integral unit on the fitting in a first rotational direction and preventing rotation of the integral unit on the fitting in a second rotational direction;

wherein application of the integral unit to the fitting engages the radial lug with the threads on the fitting; and rotation of the cap on the fitting in the second rotational direction severs the frangible attachment, thereby defining the cap and crown as separate pieces.

13. The tamper evident closure assembly of claim 12, wherein the frangible attachment is a prong including a base formed on the crown and a lateral arm extending from the crown to the cap.

14. The tamper evident closure assembly of claim 13, wherein the frangible attachment includes at least two prongs, each including a base formed on the crown and a lateral arm extending from the crown to the cap.

15. The tamper evident closure assembly of claim 13, wherein the prong includes a notch configured to break when the cap is rotated on the fitting in the second rotational direction.

16. The tamper evident closure assembly of claim 15, wherein the notch is oriented laterally toward the second rotational direction.

17. The tamper evident closure assembly of claim 12, wherein:
application of the integral unit to the fitting forms a fluid seal between the cap and the post; and
the frangible attachment is configured to sever when the fluid seal is tampered.

18. The tamper evident closure assembly of claim 12, further comprising an inner surface of the cap which is conically tapered from a bottom of the cap toward a top of the cap.

19. The tamper evident closure assembly of claim 12, wherein during application of the integral unit to the fitting, the pawl is disposed among the splines when the post and the cap form a fluid seal.

20. The tamper evident closure assembly of claim 12, wherein the pawl includes:
a ramped surface oriented acutely with respect to an inner surface of the crown;
a blunt end extending back from the ramped surface toward the inner surface of the crown transverse to the ramped surface; and
the ramped surface is directed toward the first rotational direction and the blunt end is directed toward the second rotational direction.

21. The tamper evident closure assembly of claim 12, wherein the frangible attachment is visible from outside of the assembly.

22. A tamper evident closure assembly for use with a fitting, the fitting including an outer sidewall with internally-directed threads, externally-directed splines, and a coaxial open post, the closure assembly comprising:

a cap, a crown encircling the cap and spaced apart from the cap, and a frangible attachment extending between the cap and the crown and coupling the cap to the crown, wherein the cap, crown, and frangible attachment are formed integrally as an integral unit;

an outwardly-directed lug on the cap for rotatably engaging with the threads on the fitting, wherein the radial lug is positioned below the frangible attachment;

an inwardly-directed pawl on the crown for allowing rotation of the integral unit in a first rotational direction and preventing rotation of the integral unit on the fitting in a second rotational direction, the pawl axially spaced apart from a bottom of the crown;

wherein application of the integral unit to the fitting engages the radial lug with the threads on the fitting; and rotation of the cap on the fitting in the second rotational direction severs the frangible attachment, thereby defining the cap and crown as separate pieces.

23. The tamper evident closure assembly of claim 22, wherein the frangible attachment is a prong including a base formed on the crown and a lateral arm extending from the crown to the cap.

24. The tamper evident closure assembly of claim 23, wherein the frangible attachment includes at least two prongs, each including a base formed on the crown and a lateral arm extending from the crown to the cap.

25. The tamper evident closure assembly of claim 23, wherein the prong includes a notch configured to break when the cap is rotated on the fitting in the second rotational direction.

26. The tamper evident closure assembly of claim 25, wherein the notch is oriented laterally toward the second rotational direction.

27. The tamper evident closure assembly of claim 22, wherein:
application of the integral unit to the fitting forms a fluid seal between the cap and the post; and
the frangible attachment is configured to sever when the fluid seal is tampered.

28. The tamper evident closure assembly of claim 22, further comprising an inner surface of the cap which is conically tapered from a bottom of the cap toward a top of the cap.

29. The tamper evident closure assembly of claim 22, wherein during application of the integral unit to the fitting, the pawl is disposed among the splines when the post and the cap form a fluid seal.

30. The tamper evident closure assembly of claim 22, wherein the pawl includes:
a ramped surface oriented acutely with respect to an inner surface of the crown;
a blunt end extending back from the ramped surface toward the inner surface of the crown transverse to the ramped surface; and
the ramped surface is directed toward the first rotational direction and the blunt end is directed toward the second rotational direction.

31. The tamper evident closure assembly of claim 22, wherein the frangible attachment is visible from outside of the assembly.

* * * * *